US011052192B2

(12) United States Patent
Deck et al.

(10) Patent No.: US 11,052,192 B2
(45) Date of Patent: Jul. 6, 2021

(54) DISPOSABLE INSERTER AND REUSABLE INSERTER FOR ACCOMMODATING A DISPOSABLE INSERTER

(71) Applicant: ROCHE DIABETES CARE, INC., Indianapolis, IN (US)

(72) Inventors: Frank Deck, Niederkirchen (DE); Christian Hoerauf, Oftersheim (DE); Ahmet Konya, Ludwigshafen (DE); Thomas Weiss, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 12 days.

(21) Appl. No.: 15/815,412

(22) Filed: Nov. 16, 2017

(65) Prior Publication Data

US 2018/0140769 A1 May 24, 2018

(30) Foreign Application Priority Data

Nov. 18, 2016 (EP) ..................................... 16199621

(51) Int. Cl.
*A61M 5/158* (2006.01)
*A61M 5/142* (2006.01)
(Continued)

(52) U.S. Cl.
CPC ........ *A61M 5/158* (2013.01); *A61M 5/14248* (2013.01); *A61M 5/162* (2013.01);
(Continued)

(58) Field of Classification Search
CPC .............. A61M 5/158; A61M 5/14248; A61M 2005/1585; A61M 2005/14252; A61M 2005/14268
(Continued)

(56) References Cited

U.S. PATENT DOCUMENTS

2008/0319414 A1* 12/2008 Yodfat .................. A61M 5/422
604/506
2011/0054400 A1* 3/2011 Chong .................. A61M 5/158
604/131
(Continued)

FOREIGN PATENT DOCUMENTS

| DE | 102013224431 A1 | 5/2015 |
| EP | 2433663 A1 | 3/2012 |
| EP | 2667913 B1 | 7/2016 |
| WO | WO 02081012 A2 | 10/2002 |

(Continued)

OTHER PUBLICATIONS

Extended European Search Report, EP 16199621, dated Apr. 10, 2017, 13 pages.

*Primary Examiner* — Brandy S Lee
*Assistant Examiner* — Nidah M Hussain
(74) *Attorney, Agent, or Firm* — Bose McKinney & Evans LLP

(57) ABSTRACT

This disclosure teaches a disposable inserter which includes a housing having arranged in a displaceable configuration an inserter assembly comprising a cannula assembly with a cannula, a manually operable member for displacing the inserter assembly from a retracted position to an advanced position in order to manually insert the cannula into the skin of a patient, a locking element for blocking or enabling displacement of the inserter assembly, and a coupling arrangement for coupling the disposable inserter to a reusable inserter for automatically displacing the inserter assembly from the retracted position to the advanced position in order to automatically insert the cannula into the skin of the patient.

24 Claims, 14 Drawing Sheets

(51) Int. Cl.
  *A61M 5/162* (2006.01)
  *A61M 5/14* (2006.01)
  *A61M 5/31* (2006.01)
  *A61M 5/34* (2006.01)

(52) U.S. Cl.
  CPC ......... *A61M 5/1413* (2013.01); *A61M 5/3134* (2013.01); *A61M 5/34* (2013.01); *A61M 2005/14252* (2013.01); *A61M 2005/14268* (2013.01); *A61M 2005/1585* (2013.01)

(58) Field of Classification Search
  USPC ....................................................... 604/131
  See application file for complete search history.

(56) References Cited

U.S. PATENT DOCUMENTS

| | | | |
|---|---|---|---|
| 2011/0178461 A1* | 7/2011 | Chong | A61M 5/158 604/151 |
| 2012/0078216 A1* | 3/2012 | Smith | A61M 5/1452 604/500 |
| 2012/0136300 A1* | 5/2012 | Schoonmaker | A61M 5/46 604/117 |
| 2014/0074032 A1 | 3/2014 | Bornhoft | |
| 2015/0174319 A1 | 6/2015 | Rieck | |
| 2016/0345876 A1 | 12/2016 | Fritz et al. | |

FOREIGN PATENT DOCUMENTS

| | | |
|---|---|---|
| WO | WO 2009/001345 A1 | 12/2008 |
| WO | WO 2009/010399 A1 | 1/2009 |
| WO | WO 2013/182321 A1 | 12/2013 |

\* cited by examiner

DISPOSABLE INSERTER AND REUSABLE INSERTER FOR ACCOMMODATING A DISPOSABLE INSERTER

RELATED APPLICATIONS

This application claims priority to EP 16 199 621.0, filed Nov. 18, 2016, the entire disclosure of which is hereby incorporated herein by reference.

BACKGROUND

The present invention relates to a disposable inserter and relates further to a reusable inserter for accommodating a disposable inserter.

Infusion systems enable continuous administration of liquid medicaments to patients. For example, in insulin therapies, insulin pumps enable administration of insulin to patients. Infusion systems comprise several components, wherein some components have a reusable design and other components have a disposable design. The infusion set is the component of an infusion system which establishes a fluidic connection to the body tissue. The infusion set can include a subcutaneous cannula, an adhesive mount, and a connector for connecting the infusion pump. Infusion sets usually have a disposable, single-use design, in particular for hygienic reasons. Infusion systems can include a so-called conventional pump or a so-called patch pump. The patch pump is also called a micro-pump in the following disclosure.

In case of a conventional pump, the conventional pump is spatially separated from the infusion set, wherein a tube provides a fluidic connection from the conventional pump to the infusion set. Infusion systems with a conventional pump are known for example with the type designation Accu-chek® Spirit.

In case of a micro-pump, the micro-pump is directly attached to the infusion set, wherein the fluidic connection from the micro-pump and the infusion set is not visible to the patient. Infusion systems with a micro-pump are known for example with the type designation Omnipod or Medingo Solo.

The micro-pump has the advantage over the conventional pump of a compact and comfortable design.

In case of conventional pumps it is known to apply an infusion set either manually or with the aid of an insertion device. In case of micro-pumps, insertion of the infusion set requires an insertion device. The infusion system may have an integrated insertion device, which is the case for example for the Omnipod pump.

The patient applies the infusion set autonomously. Typically, the patient replaces the infusion set about every three days. However, in case of an unexpected occlusion in the infusion set, the patient must replace the infusion set immediately in order to maintain an adequate therapy. Therefore, in daily life, the patient has to carry with him or her at all times a replacement infusion set. In the case of micro-pumps, the patient must also carry with him or her at all times an insertion device because an insertion device is required in the case of micro-pumps. The insertion devices known in the state of the art have a large design and require a bag. Therefore, the advantage of a comfortable, compact and small micro-pump is lost, because the patient has to carry at all times a large and uncomfortable insertion device with him or her.

WO2013182321A1 discloses a disposable inserter for use with an infusion device, e.g., an insulin pump. The user holds the assembly comprising the disposable inserter and a cradle by a handle protruding from the cradle and places the disposable inserter at the user's skin. The inserter is pre-loaded and the user does not have to load a cannula or to insert a cannula into the inserter. The inserter is prepared for the insertion stage by pulling a protective ring upwards, sliding it from the cylindrical portion of the disposable inserter. The user presses both buttons located on two sides of the cylindrical portion of the inserter, which initiates insertion of the cannula into the skin. The user releases the disposable inserter after insertion has been performed. The cannula was inserted into a well protruding from the cradle. The septum is parallel to the upper plane of the well, allowing connection of the micropump.

WO2009001345A1 discloses an apparatus for use with a device for delivery of a therapeutic fluid into a body of a patient. The apparatus can accommodate a subcutaneously insertable element and a penetrating member for penetrating the skin of the patient. The apparatus includes a protective member having an elongate body from which the subcutaneously insertable element and the penetrating member can be protracted to penetrate the skin and into which the penetrating member can be retracted subsequently, thereby retaining the subcutaneously insertable element in the body of the patient. A cannula cartridge unit includes a protector and a penetrating cartridge, which includes a penetrating member that pierces the skin and facilitates insertion of the cannula. The protector guards the cannula and the penetrating member. The cannula cartridge unit is either a stand-alone item, in which case the insertion can be manual, or can be loaded into an inserter. Manual insertion can be carried out using the cannula cartridge unit being a stand-alone item with the aid of a dedicated rod or by loading the cannula cartridge unit into the inserter provided with the rod. The cannula cartridge unit includes a recessed grip portion that accommodates placement of a blunt end of the rod.

WO02081012A2 discloses a device for inserting a cannula into tissues. A protective element can receive the cannula. The cannula can be removed from the protective element by an actuating element. A holding element is connected to the cannula in a fixed manner. A liquid supply line can be connected to the cannula.

WO2009010399A1 discloses an inserter device for inserting a medical device into the subcutaneous or intramuscular area of a patient. The inserter device includes means for providing a controlled and defined acceleration and deceleration of a penetrating member. A housing encompasses the penetrating member. A rotating member comprises transformation means for transforming a rotational movement into a longitudinal movement of the penetrating member. The transformation means comprises controlling means providing a controlled variation of the velocity of the penetrating member in the direction of insertion.

SUMMARY

This disclosure teaches a disposable inserter and a reusable inserter, which do not have at least some of the disadvantages of the prior art. In particular, this disclosure presents a disposable inserter for manually inserting a cannula into the skin of a patient. In particular, this disclosure teaches a reusable inserter for accommodating a disposable inserter and automatically inserting a cannula into the skin of a patient. The disposable inserter has a small and safe design.

According to this disclosure, a disposable inserter is disclosed which comprises: a housing having arranged in a displaceable configuration an inserter assembly comprising a cannula assembly with a cannula, a manually operable member for displacing the inserter assembly from a retracted position to an advanced position in order to manually insert the cannula into the skin of a patient, a locking element for blocking or enabling displacement of the inserter assembly, and a coupling arrangement for coupling the disposable inserter to a reusable inserter for automatically displacing the inserter assembly from the retracted position to the advanced position in order to automatically insert the cannula into the skin of the patient. The locking element can detect if displacement of the inserter assembly is permissible and block or enable displacement of the inserter assembly accordingly. For example, the locking element can be configured to enable displacement if the inserter assembly is correctly engaged with a baseplate of an infusion system. The coupling arrangement of the disposable inserter allows the patient to choose between manual insertion of the cannula or automatic insertion of the cannula. Thus, when the patient is for example at home with a reusable inserter available, the patient can benefit from an automatic insertion of the cannula. When the patient is for example not at home and does not have a reusable inserter available, the patient still can perform a manual insertion of the cannula, which is mandatory in case of an unexpected occlusion.

In an embodiment, an outlet port of the housing is configured to engage with a baseplate of an infusion system, the baseplate being adhered to the skin of the patient, and wherein the cannula assembly is configured to be placed through the outlet port into a well of the baseplate when the inserter assembly is displaced from the retracted position to the advanced position in order to insert the cannula into the skin of the patient. At the same time when the cannula assembly is placed into the well, the cannula is inserted into the skin of the patient. Insertion of the cannula is therefore very precise.

In an embodiment, the locking element is configured to block displacement of the inserter assembly when the disposable inserter is not engaged with a baseplate of an infusion system, and to enable displacement of the inserter assembly when the disposable inserter is engaged with the baseplate of the infusion system. When the disposable inserter is not engaged with a baseplate of an infusion system, displacement of the inserter assembly is prevented.

In an embodiment, the locking element is connected to the housing of the disposable inserter via a torsion joint, wherein the locking element is configured to move into positions in accordance to if the disposable inserter engages the baseplate of the infusion system or not, wherein the locking element is configured to block or enable operating the manually operable member accordingly. The locking element can be configured that a spring force returns the locking element into the position adapted for blocking operation of the manually operable member. By blocking the manually operable member, displacement of the inserter assembly is blocked at the same time. Blocking the manually operable member has a simple design.

In an embodiment, the inserter assembly includes a needle assembly with a needle, wherein the needle assembly is configured to engage with the cannula assembly, wherein insertion of the cannula into the skin of the patient is supported by the needle. The needle can support a flawless insertion of the cannula into the skin of the patient.

In an embodiment, the inserter assembly is configured to be retractable from the advanced position to the retracted position, wherein the cannula is left in the skin of the patient, wherein the needle is retracted from the skin of the patient. After the cannula has been inserted into the skin of the patient, the needle has to be removed such that a medicine can be transported via a duct of the cannula from a reservoir to the patient.

In an embodiment, the inserter assembly comprises a coupling assembly for coupling the inserter assembly to the reusable inserter. The reusable inserter can be coupled both to the disposable inserter and the inserter assembly of the disposable inserter.

In an embodiment, the housing has an elongated body. An elongated body allows the inserter assembly to be displaced sufficiently enough from the retracted position to the advanced position.

In an embodiment, the manually operable member has a manually displaceable sleeve that is displaceable along the housing and engages the inserter assembly for displacing the inserter assembly from the retracted position to the advanced position. A manually displaceable sleeve has a simple design.

This disclosure further relates to a reusable inserter configured to accommodate a disposable inserter as described above, wherein the reusable inserter comprises a release for activating a drive for automatically displacing the inserter assembly of the disposable inserter from a retracted position to an advanced position in order to automatically insert the cannula into the skin of a patient. The patient can choose between manual insertion of the cannula and automatic insertion.

In an embodiment, the reusable inserter comprises tensioning equipment for tensioning a drive spring of the drive. The reusable inserter can have a purely mechanic design not requiring replacement of energy sources such as batteries.

In an embodiment, a tensioning knob of the tensioning equipment is configured to be turned by a predefined angle for tensioning the drive spring of the drive. Tension of the spring has a predefined value, wherein the displacement of the inserter assembly occurs according to predefined dynamics, i.e., acceleration, velocity, etc.

In an embodiment, the predefined angle is 360°. The tension of the spring can be brought to a high value, wherein the design of the reusable inserter can be kept simple.

In an embodiment, the tensioning equipment includes a return stop. The patient can operate the tensioning equipment in several steps and have a stop between the steps in order to grasp the reusable inserter in a new position that allows for further tensioning of the tensioning equipment.

In an embodiment, the reusable inserter is configured to accommodate the disposable inserter before, while or after tensioning of the drive spring of the drive.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
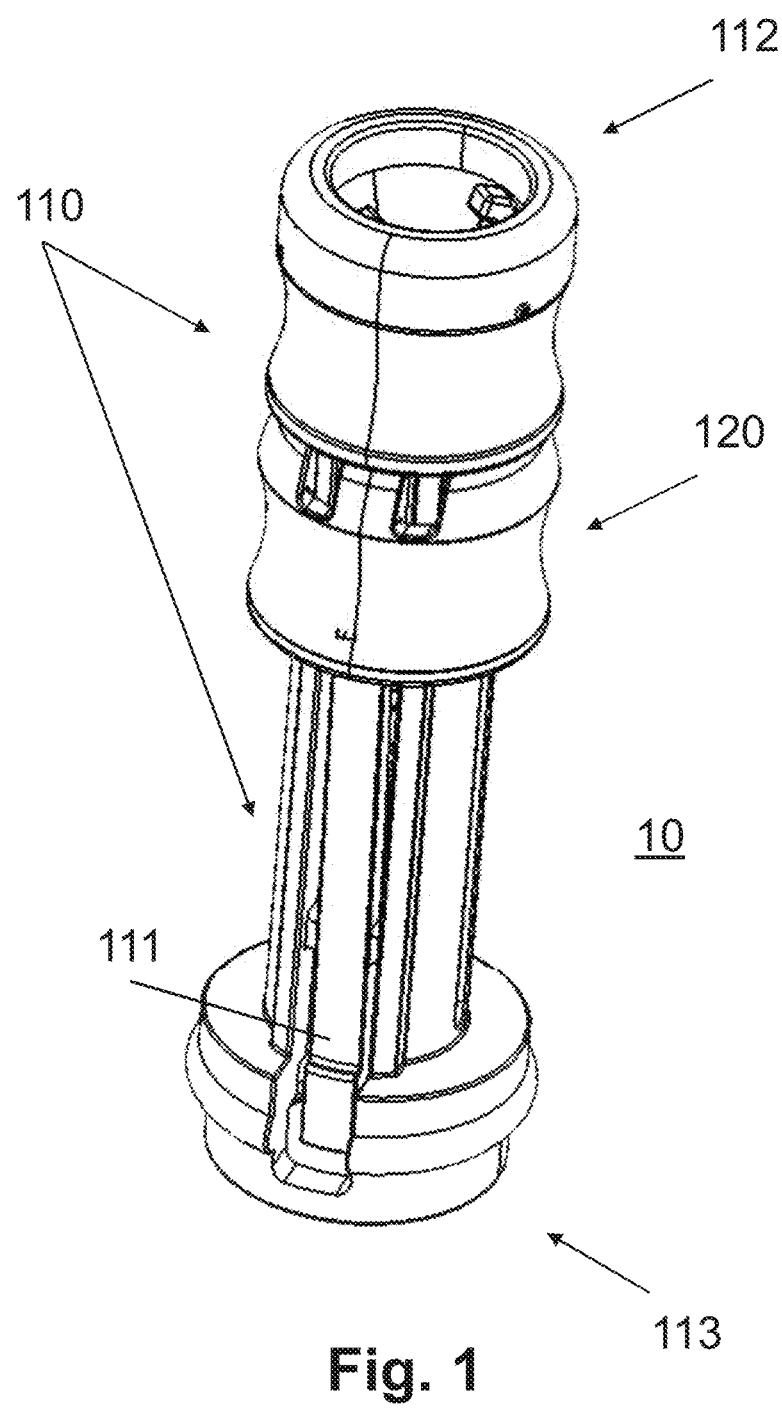
FIG. 1 schematically illustrates a perspective view of a disposable inserter.

FIG. 1 illustrates schematically a perspective view of a disposable inserter 10.

The disposable inserter 10 comprises a housing 110. The housing 110 has arranged in a displaceable manner an inserter assembly (not illustrated in FIG. 1) comprising a cannula assembly with a cannula (not illustrated in FIG. 1).

The disposable inserter 10 comprises a manually operable member 120. The manually operable member 120 is configured to displace the inserter assembly (not illustrated in FIG. 1) from a retracted position to an advanced position (not illustrated in FIG. 1) in order to insert the cannula into the skin of a patient (not illustrated in FIG. 1).

The disposable inserter 10 comprises a locking element or lock 111 configured to prevent inadvertent displacement of the inserter assembly.

The disposable inserter 10 comprises a coupling arrangement or coupler 112. The coupling arrangement 112 is configured to couple the disposable inserter to a reusable inserter (not illustrated in FIG. 1) for automatically displacing the inserter assembly from the retracted position to the advanced position.

As illustrated in FIG. 1, the disposable inserter 10 can comprise an outlet port 113. The outlet port 113 is configured to engage with a baseplate of an infusion system (not illustrated in FIG. 1). The baseplate is adhered to the skin of the patient (not illustrated in FIG. 1). The cannula assembly is configured to be placed through the outlet port 113 into a well of the baseplate by displacing the inserter assembly from the retracted position to the advanced position in order to insert the cannula into the skin of the patient (not illustrated in FIG. 1).

Figure 2:
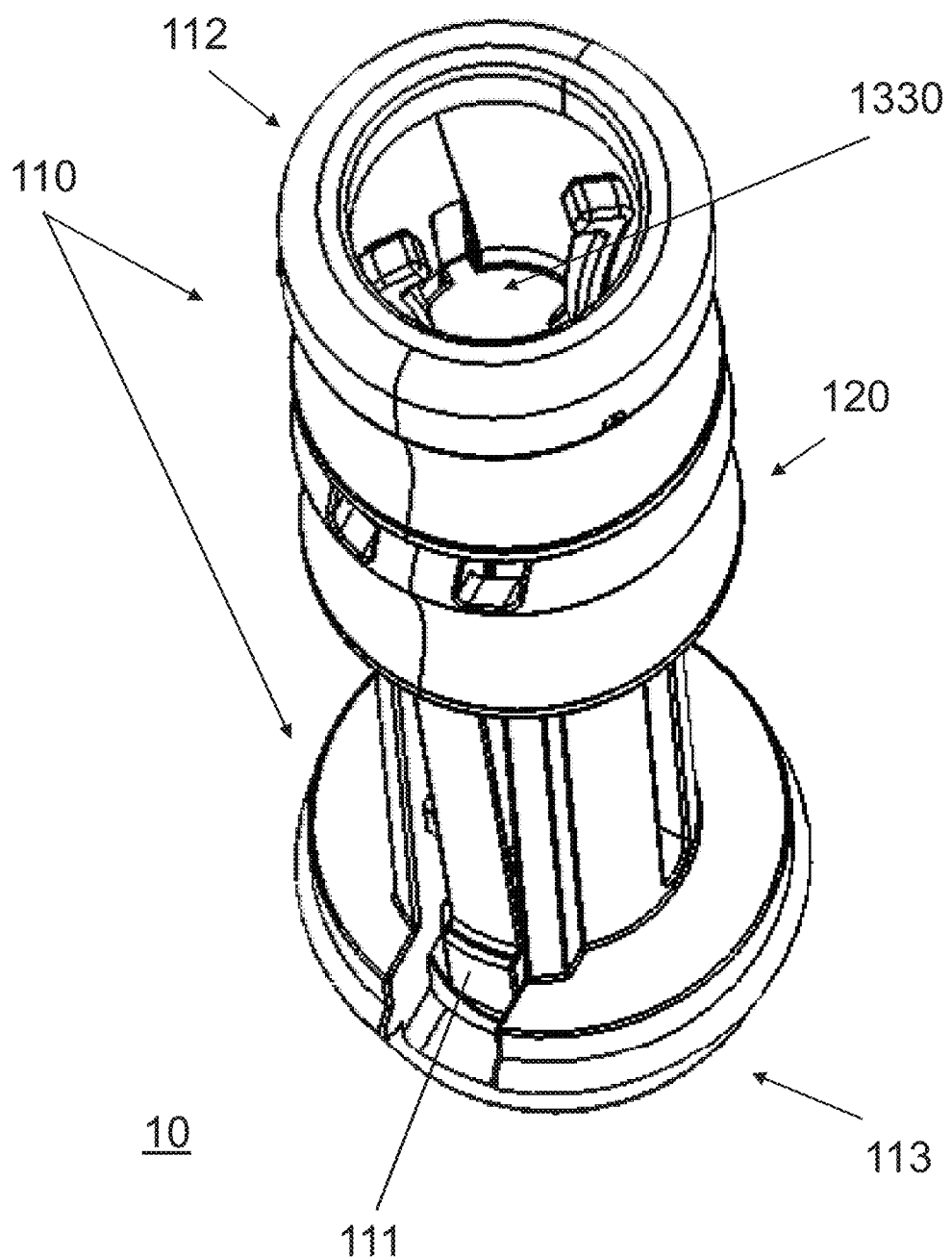
FIG. 2 schematically illustrates another perspective view of the disposable inserter.

FIG. 2 illustrates schematically another perspective view of the disposable inserter 10.

The disposable inserter 10 comprises the housing 110, the manually operable member 120, the locking element 111, and the coupling arrangement 112. The disposable inserter can comprise an outlet port 113. As illustrated in FIG. 2, the coupling arrangement 112 can provide access to a coupling assembly 1330 of the inserter assembly.

Figure 3:
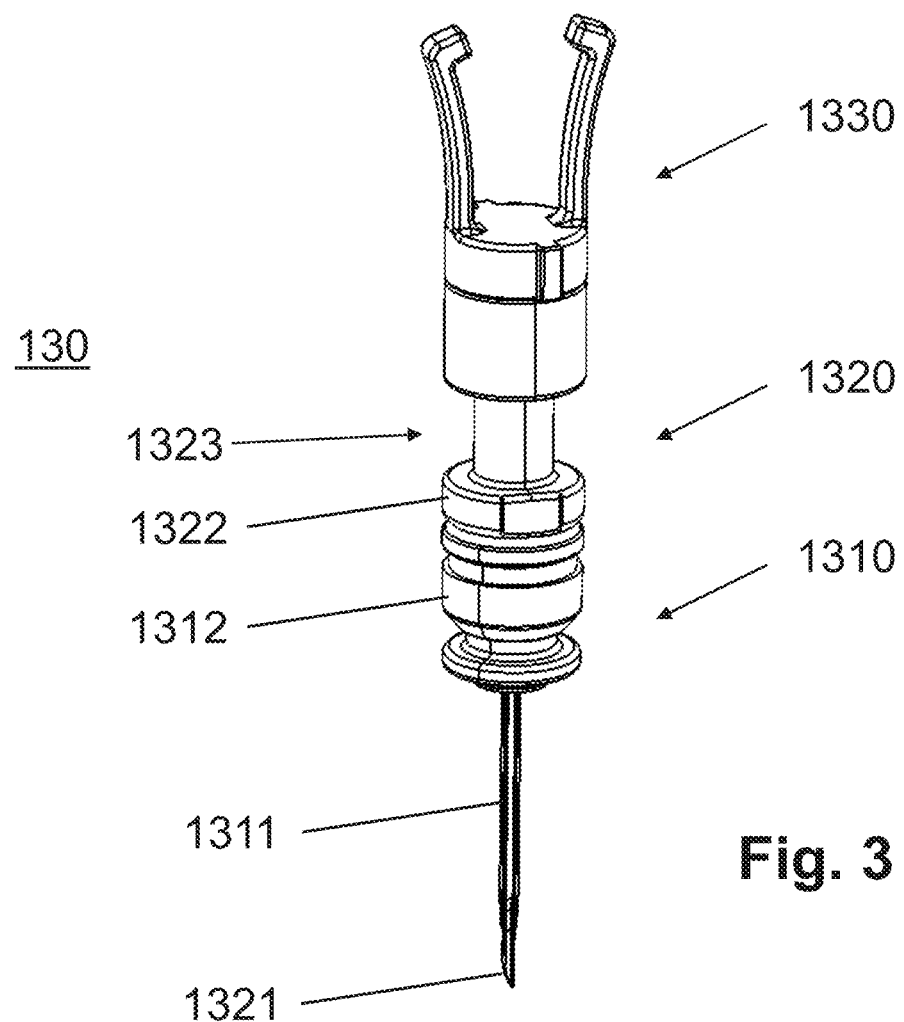
FIG. 3 schematically illustrates a perspective view of the inserter assembly of the disposable inserter.

FIG. 3 illustrates schematically a perspective view of the inserter assembly 130 which is arranged in a displaceable manner in the housing 110 of the disposable inserter 10.

The inserter assembly 130 comprises a cannula assembly 1310, a needle assembly 1320, and a coupling assembly 1330. The cannula assembly 1310 comprises a cannula 1311 and a cannula hub 1312. The needle assembly 1320 comprises a needle 1321 and a needle hub 1322. The needle 1321 can be configured to enable flawless penetration of the skin of the patient. The needle 1321 can be configured to support insertion of the cannula 1311 into the skin of the patient. The needle 1321 can extend through the cannula 1311. The needle 1321 and the cannula 1311 can have a design such that displacement of the needle 1321 with respect to the cannula 1311 is enabled.

The inserter assembly 130 can be displaced from a retracted position to an advanced position. The advanced position is in the direction of the tip of the needle 1321. The retracted position is in the opposite direction. In the advanced position, the needle 1321 and the cannula 1311 can have been inserted into the skin of the patient. The needle assembly 1320 can be retracted separate from the cannula assembly 1310, wherein the needle 1321 is retracted from the skin of the patient and the cannula 1311 is left in the skin of the patient. For example, the needle assembly 1320 and the coupling assembly can be retracted together.

The cannula hub 1312 can be configured to be placed into a well of a baseplate of an infusion system, the baseplate being adhered to the skin of the patient, wherein the cannula is configured for being inserted in the skin of the patient when the cannula hub 1312 is placed in the well of the baseplate of the infusion system.

The needle assembly 1320 can comprise a recess 1323 configured to engage with the manually operable member 120 for enabling manual displacement of the inserter assembly from the retracted position to the advanced position in order to insert the cannula into the skin of the patient. The manually operable member 120 can be configured for being displaced from a retracted position, as illustrated in FIG. 1 and FIG. 2, to an advanced position (not illustrated in FIG. 1 and FIG. 2), wherein because of the engagement with the recess 1323 of the needle assembly 1320, the inserter assembly 130 is displaced from the retracted position to the advanced position, wherein the needle 1321 penetrates the skin of the patient, and wherein the cannula 1311 is inserted into the skin of the patient. The manually operable member 120 can be configured for being displaced from the advanced position, as described before, to the retracted position, as illustrated in FIG. 1 and FIG. 2. The cannula assembly 1310 and the needle assembly 1320 can be configured such that because of the engagement with the recess 1323 of the needle assembly 1320, not the whole inserter assembly 130 is displaced from the advanced position to the retracted position, but only the needle assembly 1320 together with the coupling assembly 1330 are displaced from the advanced position to the retracted position, wherein the needle 1321 is withdrawn from the skin of the patient, and wherein the cannula 1311 is left in the skin of the patient.

Figure 4:
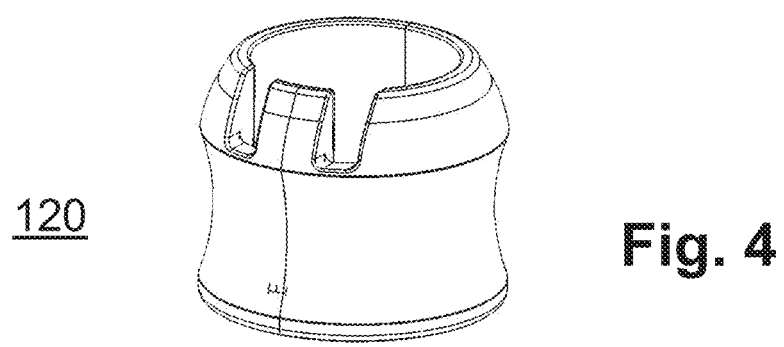
FIG. 4 schematically illustrates a perspective view of a manually operable member of the disposable inserter.

FIG. 4 illustrates schematically a perspective view of a manually operable member or handle 120 of the disposable inserter 10. The manually operable member 120 is configured to displace the inserter assembly from a retracted position to an advanced position. The manually operable member 120 can further be configured to displace at least a part of the inserter assembly from the advanced position to the retracted position. As illustrated in FIG. 4, the manually operable member 120 can include an arcuate surface such that a patient can firmly operate the manually operable member. The manually operable member 120 can include one or more protrusions (not illustrated in FIG. 4) for enabling engagement with the recess 1323 of the needle assembly 1320.

Figure 5:
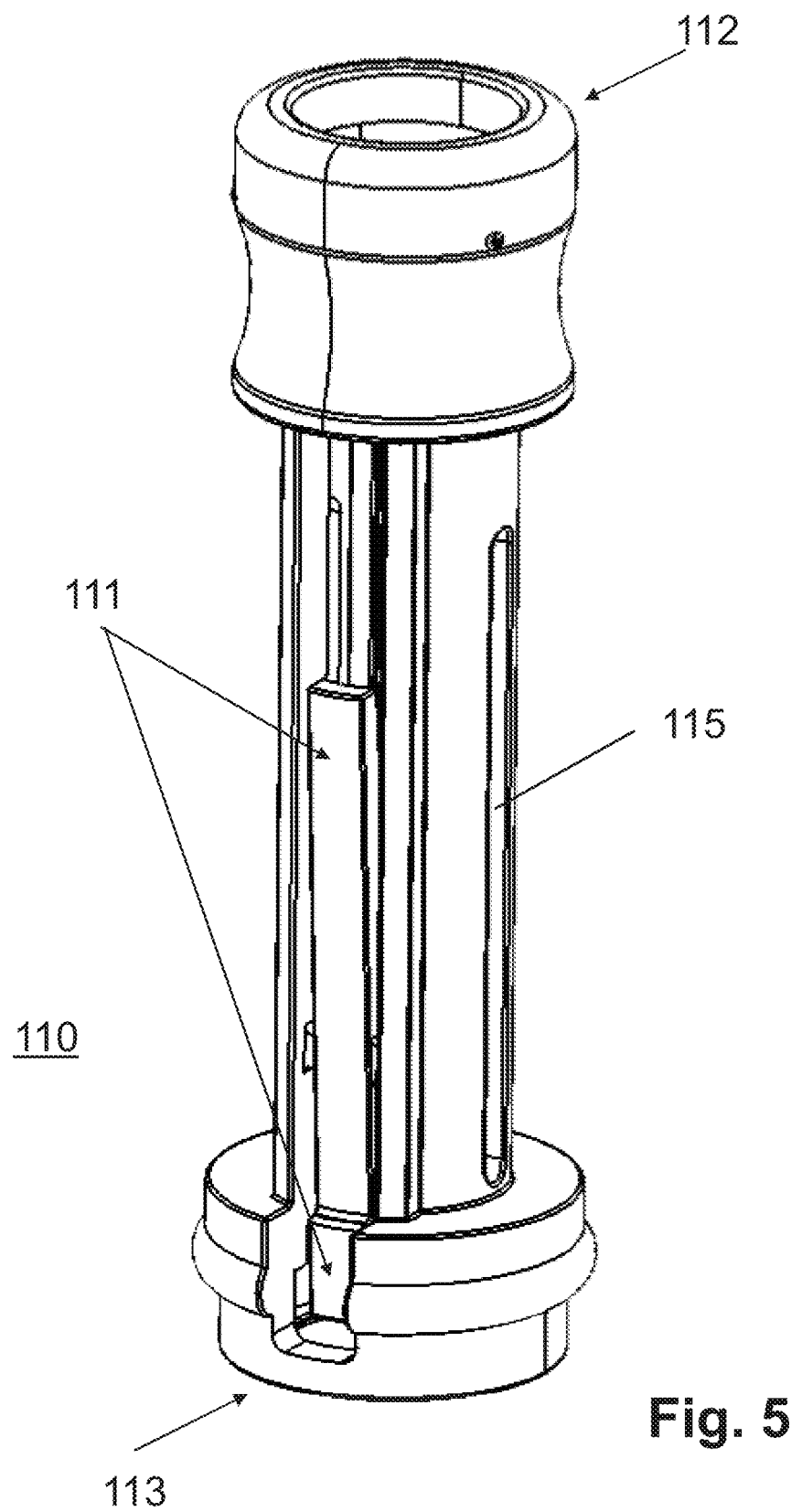
FIG. 5 schematically illustrates a perspective view of the housing of the disposable inserter.

FIG. 5 illustrates schematically a perspective view of the housing 110 of the disposable inserter 10. The housing 110 has arranged in a displaceable manner the inserter assembly 130 (not illustrated in FIG. 5). As illustrated in FIG. 5, the housing 110 can have the design of an elongated body. The housing 110 can have a cylindrical design. As illustrated in FIG. 5, the housing 110 can support the locking element 111. The locking element 111 can extend from the outlet port 113 to a region of the housing where the manually operable member 120 is arranged in the retracted position. The housing 110 can include a guiding groove 115 for guiding the manually operable member 120. The guiding groove 115 can enable the manually operable member 120 to engage with the inserter assembly 130. As illustrated in FIG. 5, the coupling arrangement 112 can include an arcuate surface such that a patient can firmly grasp the housing 110, in particular in order to enable firm operation of the manually operable member 120.

Figure 6:
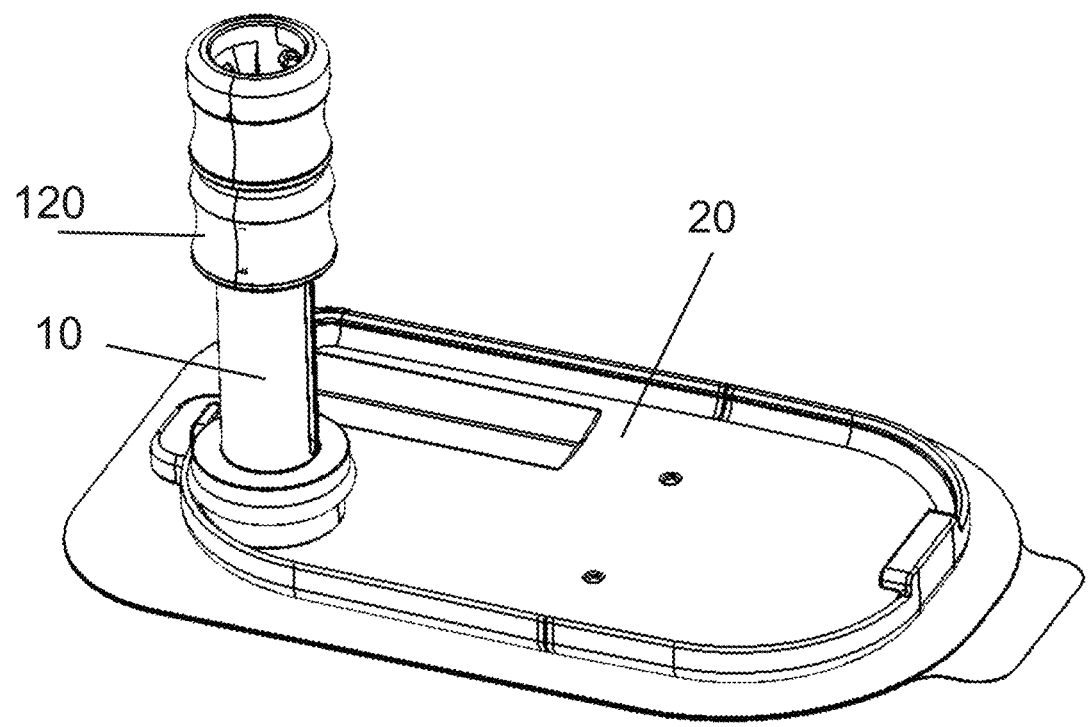
FIG. 6 schematically illustrates a perspective view of a disposable inserter that engages a baseplate of an infusion system.

FIG. 6 illustrates schematically a perspective view of a disposable inserter 10 that engages a baseplate 20 of an infusion system, for example the baseplate 20 that is configured to receive a micro-pump. The baseplate 20 can be adhered to the skin of a patient. The baseplate 20 can include a well (not shown in FIG. 6) that is configured to engage with the outlet port 113 of the disposable inserter 10. As illustrated in FIG. 6, the disposable inserter 10 comprises a manually operable member 120 for displacing the inserter assembly of the disposable inserter 10 from a retracted position, which is illustrated in FIG. 6, to an advanced position (not illustrated in FIG. 6), wherein the cannula hub 1312 is placed into the well of the baseplate 20, and wherein the cannula 1311 is inserted into the skin of the patient, possibly with the support of a needle 1321 that enables flawless penetration of the skin of the patient.

Figure 7:
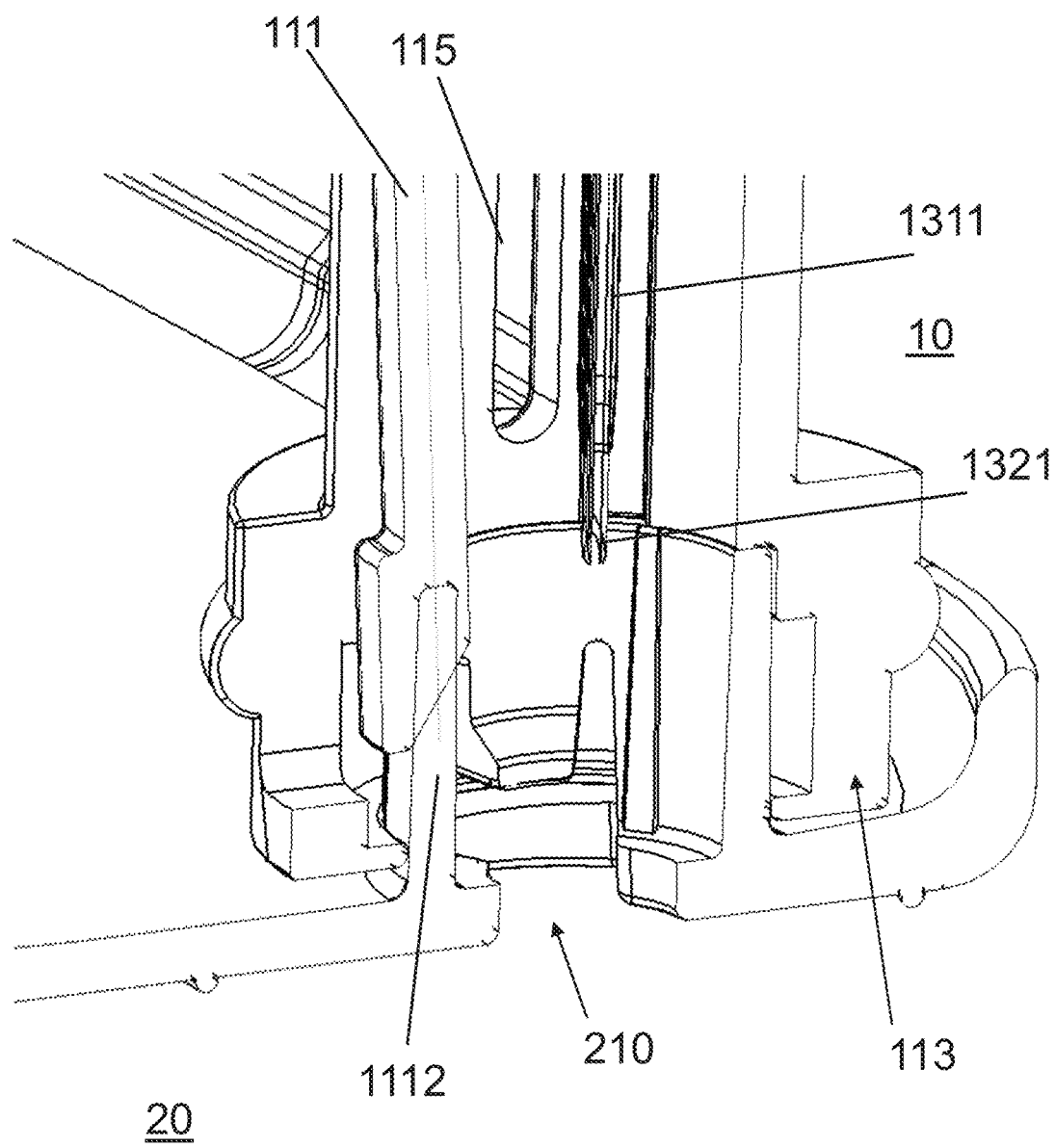
FIG. 7 schematically illustrates a sectional view of a disposable inserter that engages with a baseplate of an infusion system.

FIG. 7 illustrates schematically a sectional view of a disposable inserter 10 that engages with a baseplate 20. In particular, an outlet port 113 of the disposable inserter 10 engages with a well 210 of the baseplate 20. The outlet port 113 and the well 210 have a cylindrical design that is matched with each other. The outlet port 113 and the well 210 can be designed that the disposable inserter 10 engages firmly with the baseplate 20, for example via a press fit, a snap mechanism, etc. As illustrated in FIG. 7, the locking element 111 interacts with the outlet port 113 in order to detect if the disposable inserter 10 engages with the baseplate 20 or not. In particular, a lower end 1112 of the locking element 111 detects if the disposable inserter 10 engages with the baseplate 20.

Figure 8:
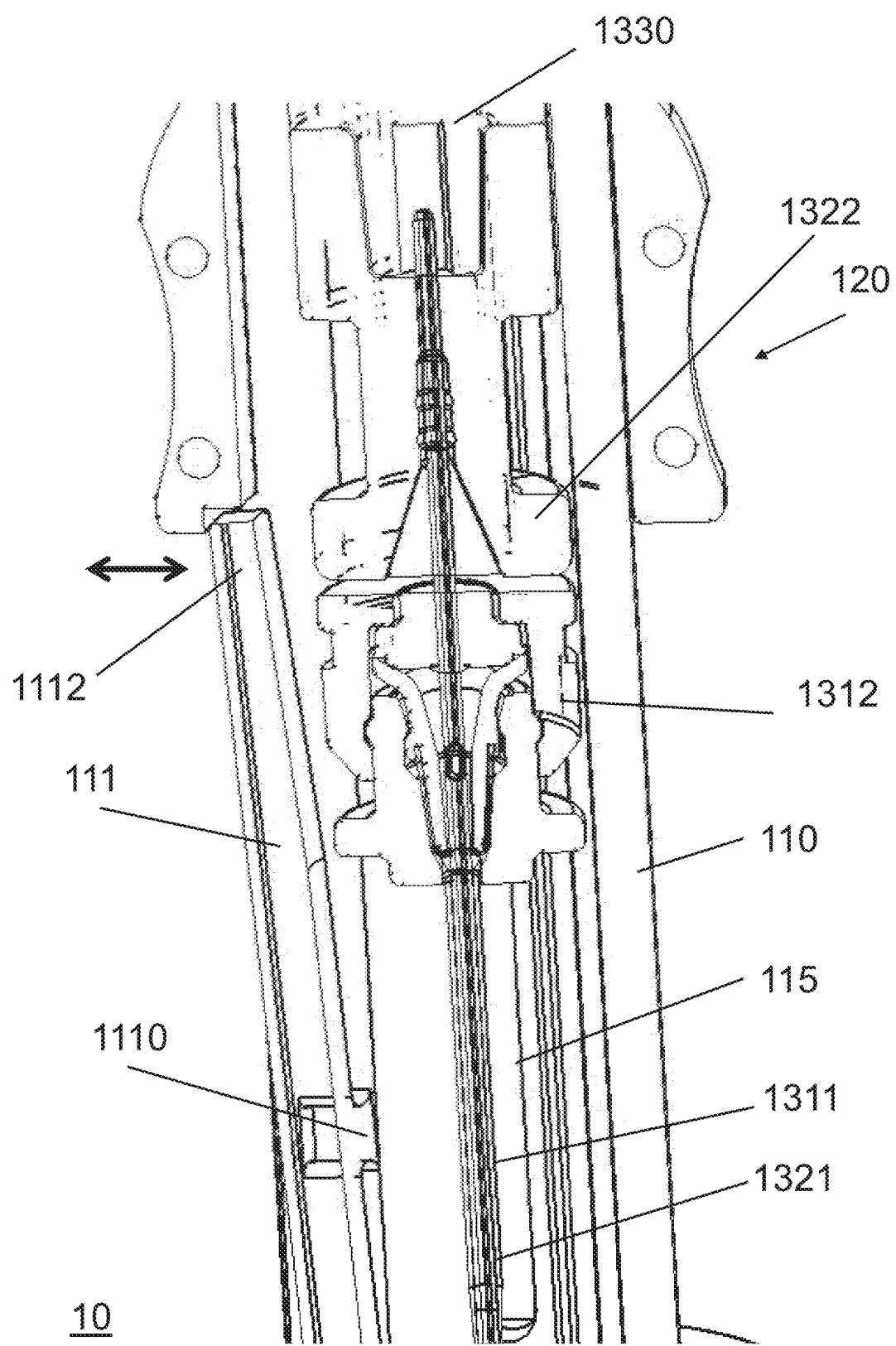
FIG. 8 schematically illustrates a sectional view of a disposable inserter.

FIG. 8 illustrates schematically a sectional view of a disposable inserter 10. The disposable inserter 10 has a housing 110 that accommodates the inserter assembly 130 which comprises the cannula assembly 1310 with the cannula hub 1312 and the cannula 1311, the needle assembly 1320 with the needle hub 1322 and the needle 1321, and the coupling assembly 1330. A manually operable member 120 enables that the inserter assembly 130 can be displaced from a retracted position (in upwards direction in FIG. 8) to an advanced position (in downwards direction in FIG. 8), in particular along the guiding grove 115. As illustrated in FIG. 8, a locking element 111 is arranged. The locking element 111 is connected via torsion joint 1110 with the housing 110.

In case the disposable inserter 10 is not engaged with a baseplate 20, the lower end 1111 (not shown in FIG. 8) does not interact with the baseplate 20. In this case, the locking element 111 is configured that the lower end 1111 moves towards a center of the housing 110, wherein the upper end 1112 moves away from a center of the housing 110, for example because of a respective spring force of the torsion joint 1110. The upper end 1112 of the locking element 111 abuts the manually operable member 120, wherein the manually operable member 120 is blocked from being displaced and displacement of the inserter assembly 130 towards the advanced position is prevented.

In case the disposable inserter 10 is engaged with a baseplate 20, the lower end 1111 (not shown in FIG. 8) interacts with the baseplate 20. In this case, the locking element 111 is configured that the lower end 1111 moves away from a center of the housing 110, wherein the upper end 1112 moves towards a center of the housing 110. The upper end 1112 does not abut the manually operable member 120, wherein the manually operable member 120 can be displaced in the direction downwards in FIG. 8 and displacement of the inserter assembly 130 towards the advanced position is enabled.

The cases of the disposable inserter 10 being not engaged with a baseplate 20 or being engaged with the baseplate 20 are indicated by the arrows at the upper end 1112 of the locking element 111.

Figure 9:
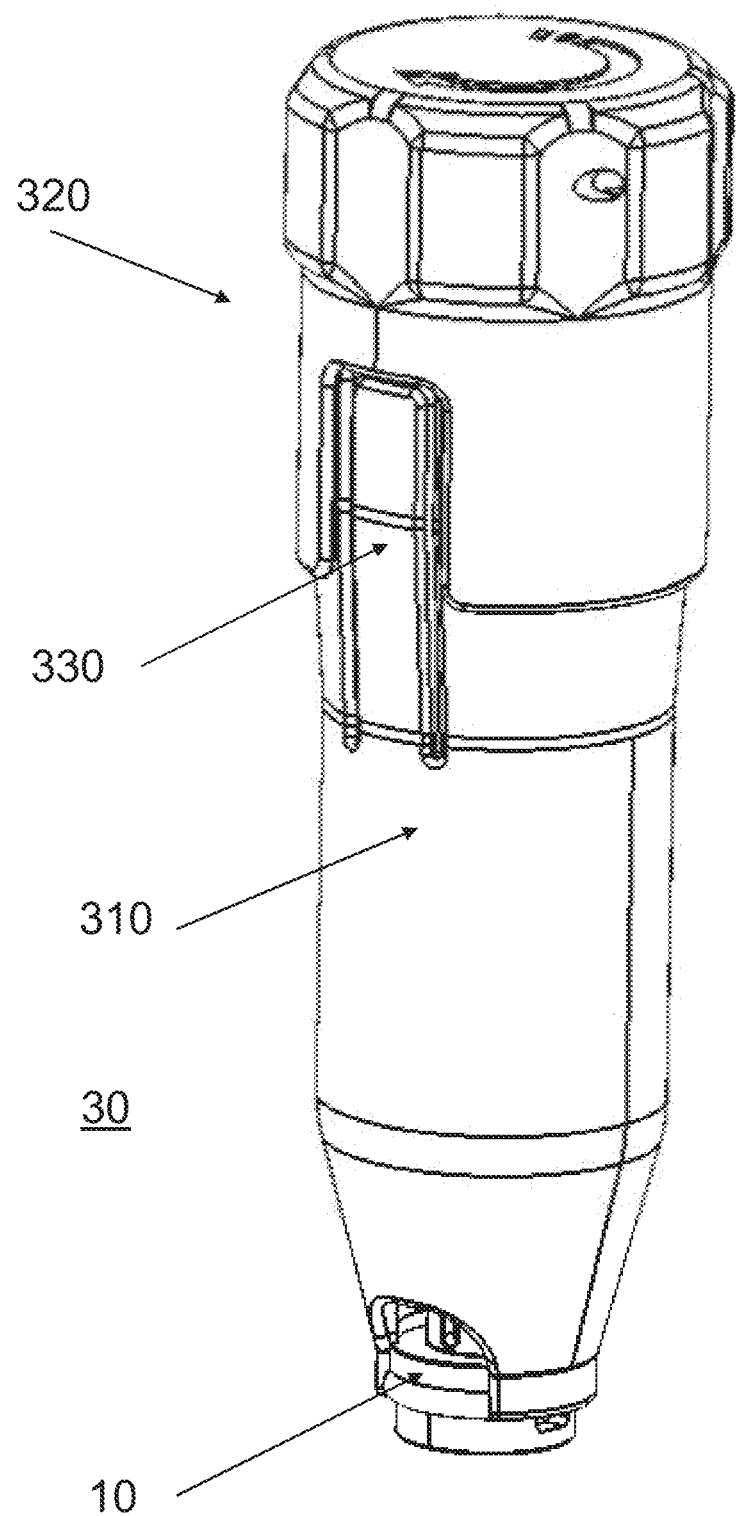
FIG. 9 schematically illustrates a perspective view of a reusable inserter.

FIG. 9 illustrates schematically a perspective view of a reusable inserter 30. The reusable inserter 30 has a housing 310, a tensioning equipment 320 and a release 330. The reusable inserter 30 accommodates a disposable inserter 10.

Figure 10:
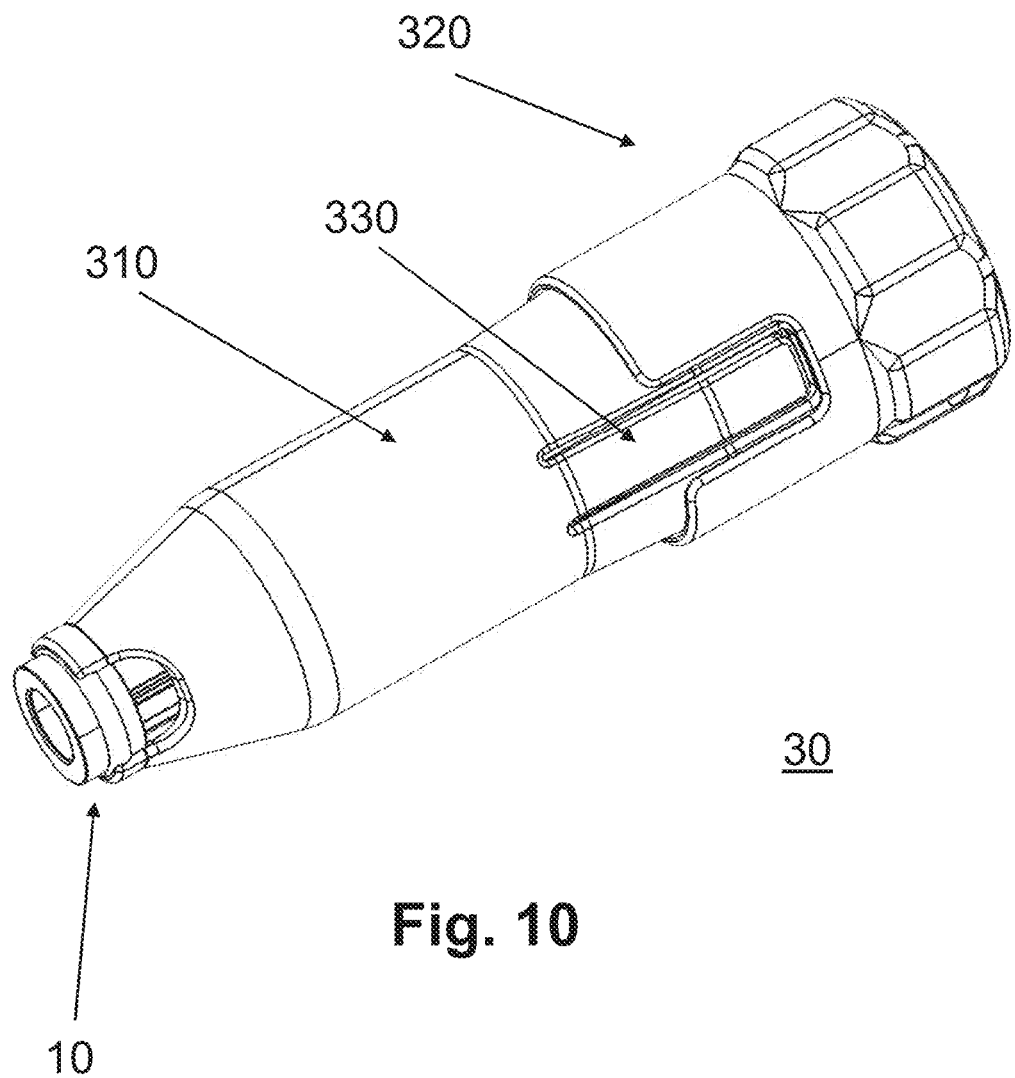
FIG. 10 schematically illustrates another perspective view of the reusable inserter.

FIG. 10 illustrates schematically another perspective view of the reusable inserter 30.

The reusable inserter 30 displaces automatically the inserter assembly 130 of the reusable inserter 30 from a retracted position to an advanced position in order to insert the cannula into the skin of a patient. The reusable inserter 30 includes a drive that is based on a rotating crank having an angle of rotation of 360°. When tensioning the reusable inserter 30, the crank remains blocked and no displacement of the inserter assembly occurs. Coupling between the reusable inserter 30 and the inserter assembly is based on a positive fitting between elastic arms and a plunger.

The tensioning equipment 320 can have a 360° design such that in order to tension the reusable inserter 30, a patient using the tensioning equipment 320 needs to turn the tensioning equipment 320 relative to the housing 310 by an angle of 360°.

The tensioning equipment 320 can include a return stop such that when a patient turns the tensioning equipment 320 relative to the housing 310 and releases the tensioning equipment 320, the tensioning equipment 320 does not return back to the initial position, but stays in the current position.

The tensioning equipment 320 can be designed that overdraw is impossible.

The release 330 can be designed that operating the release 330 is only possible if the tensioning equipment 320 has been properly manipulated by the patient, i.e., if the patient has properly turned the tensioning equipment 320 by 360°.

The disposable inserter 10 can be inserted into the reusable inserter 30 before, during or after manipulation of the tensioning equipment 320.

Figure 11:
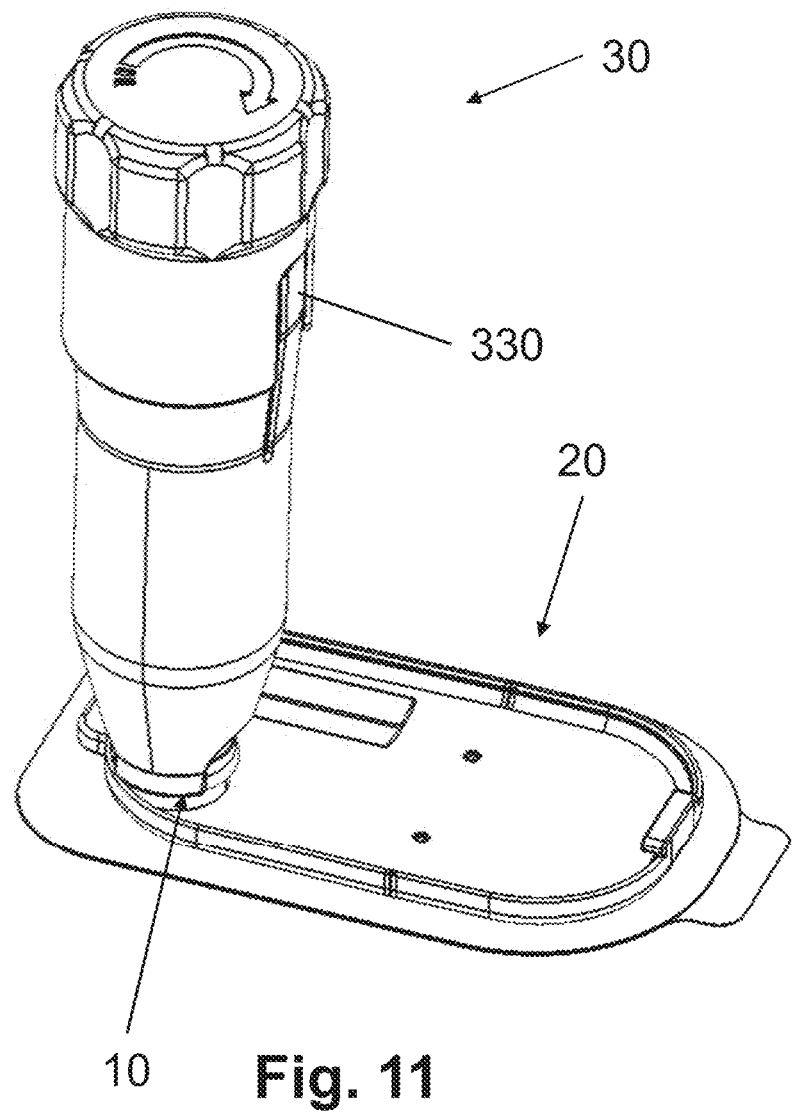
FIG. 11 schematically illustrates a perspective view of a disposable inserter which engages a baseplate of an infusion system, wherein the disposable inserter is accommodated within a reusable inserter.

FIG. 11 illustrates schematically a perspective view of a disposable inserter 10 which engages a baseplate 20 of an infusion system, wherein the disposable inserter 10 is accommodated within a reusable inserter 30. The baseplate 20 can be adhered to the skin of a patient. The patient can manipulate the release 330 of the reusable inserter 30 in order to insert the cannula into his or her skin.

Figure 12:
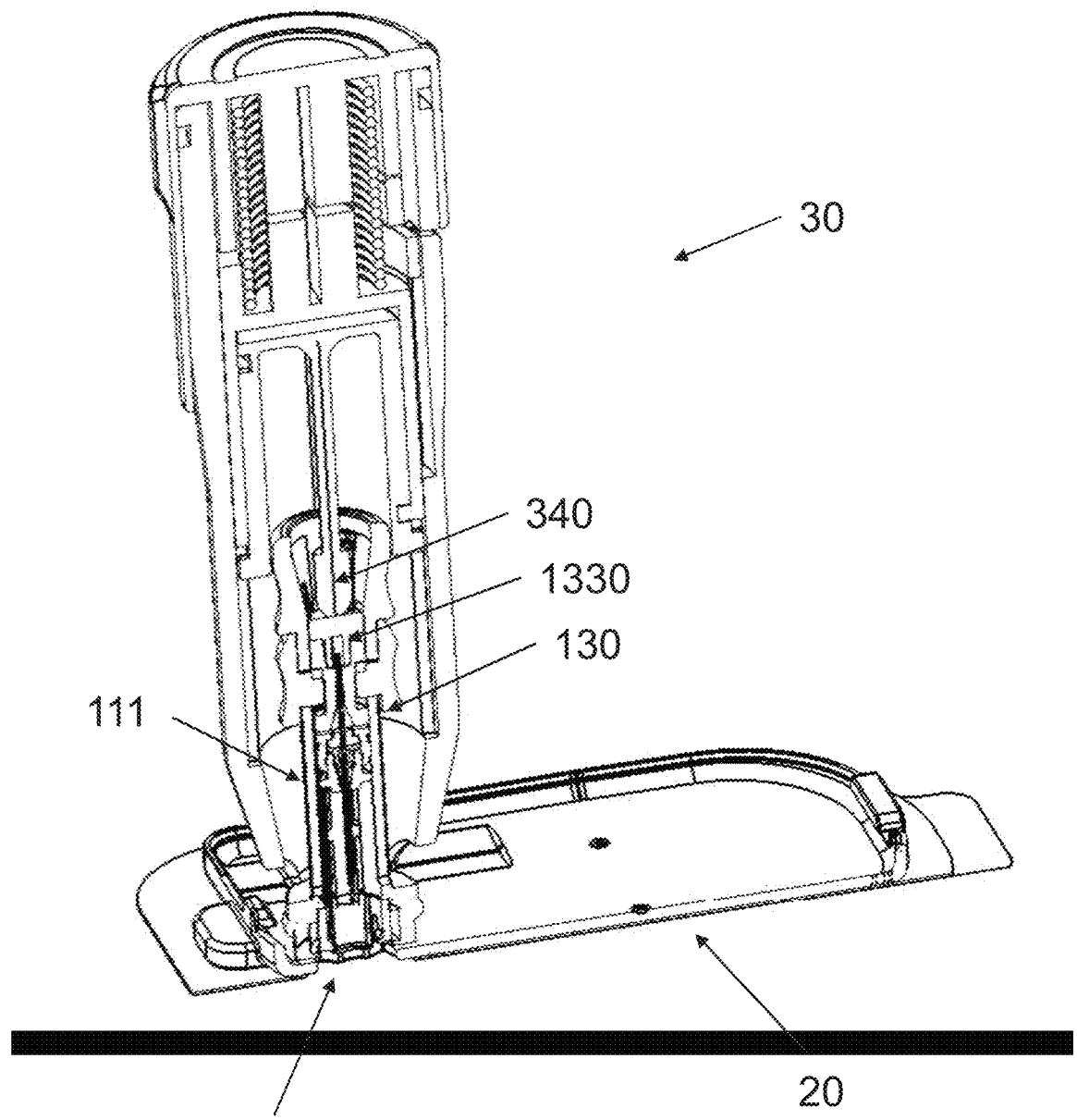
FIG. 12 schematically illustrates a sectional view of a disposable inserter which engages a baseplate of an infusion system, wherein the disposable inserter is accommodated within a reusable inserter.

FIG. 12 illustrates schematically a sectional view of a disposable inserter 10 which engages a baseplate 20 of an infusion system, wherein the disposable inserter 10 is accommodated within a reusable inserter 30. The baseplate 20 can be adhered to the skin of a patient. The disposable inserter 10 has arranged a inserter assembly 130 in a displaceable design. The disposable inserter 10 comprises a locking element 111. Because the disposable inserter 10 engages the baseplate 20, the locking element 111 enables displacement of the inserter assembly 130. The coupling assembly 1330 of the inserter assembly 130 is coupled to the plunger 340 of the reusable inserter 30. The baseplate 20 can be adhered to the skin of a patient. The patient can manipulate the release (not illustrated in FIG. 12) of the reusable inserter 30 in order to insert the cannula into his or her skin.

Figure 13:
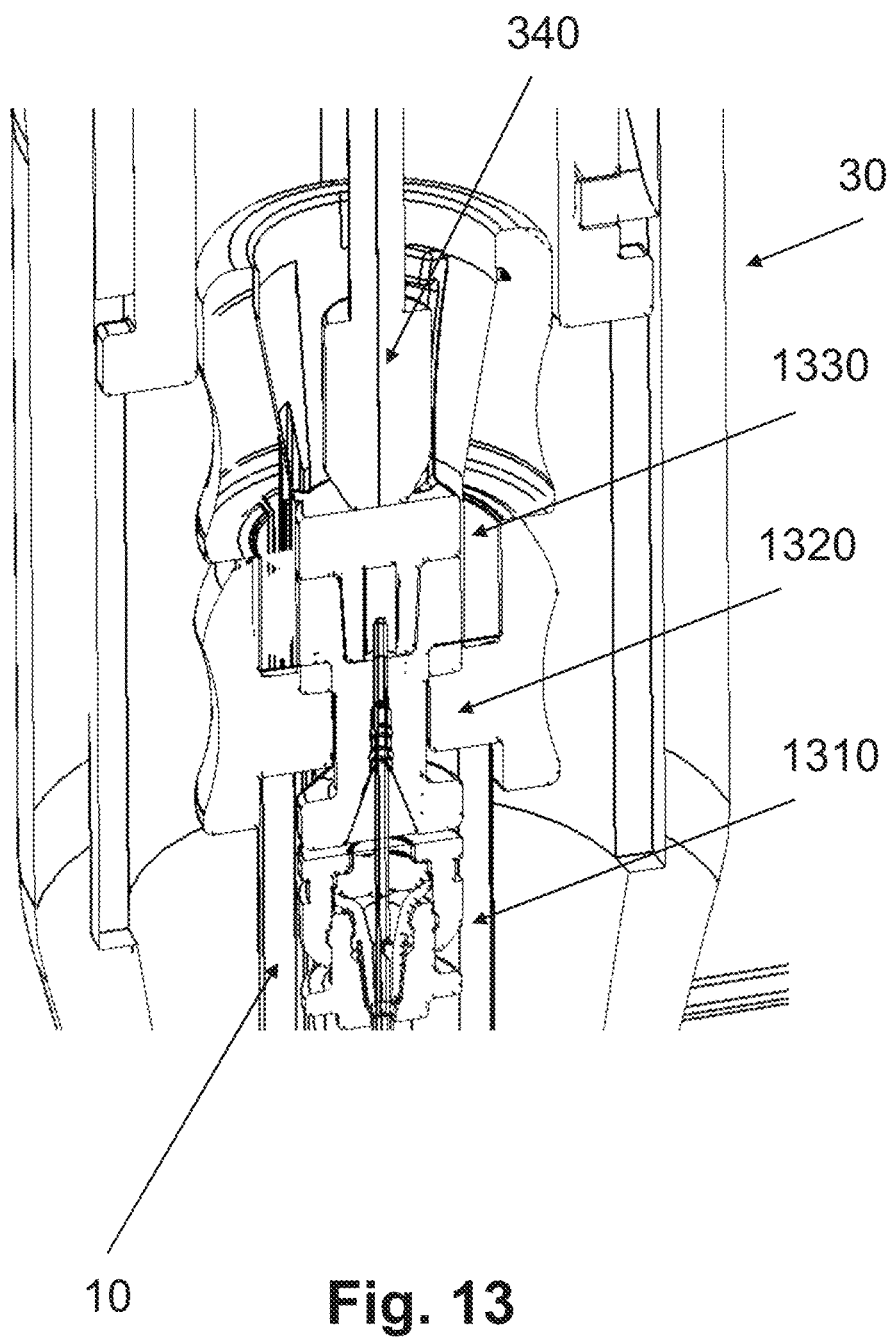
FIG. 13 schematically illustrates a sectional view of a reusable inserter which accommodates a disposable inserter.

FIG. 13 illustrates schematically a sectional view of a reusable inserter 30 which accommodates a disposable inserter 10. The disposable inserter 10 comprises an inserter assembly 130 with a cannula assembly 1310, a needle assembly 1320 and a coupling assembly 1330. The coupling assembly 1330 of the inserter assembly 130 is coupled to the plunger 340 of the reusable inserter 30 based on a positive fitting between elastic arms of the coupling assembly 1330 and a plunger 340.

Figure 14:
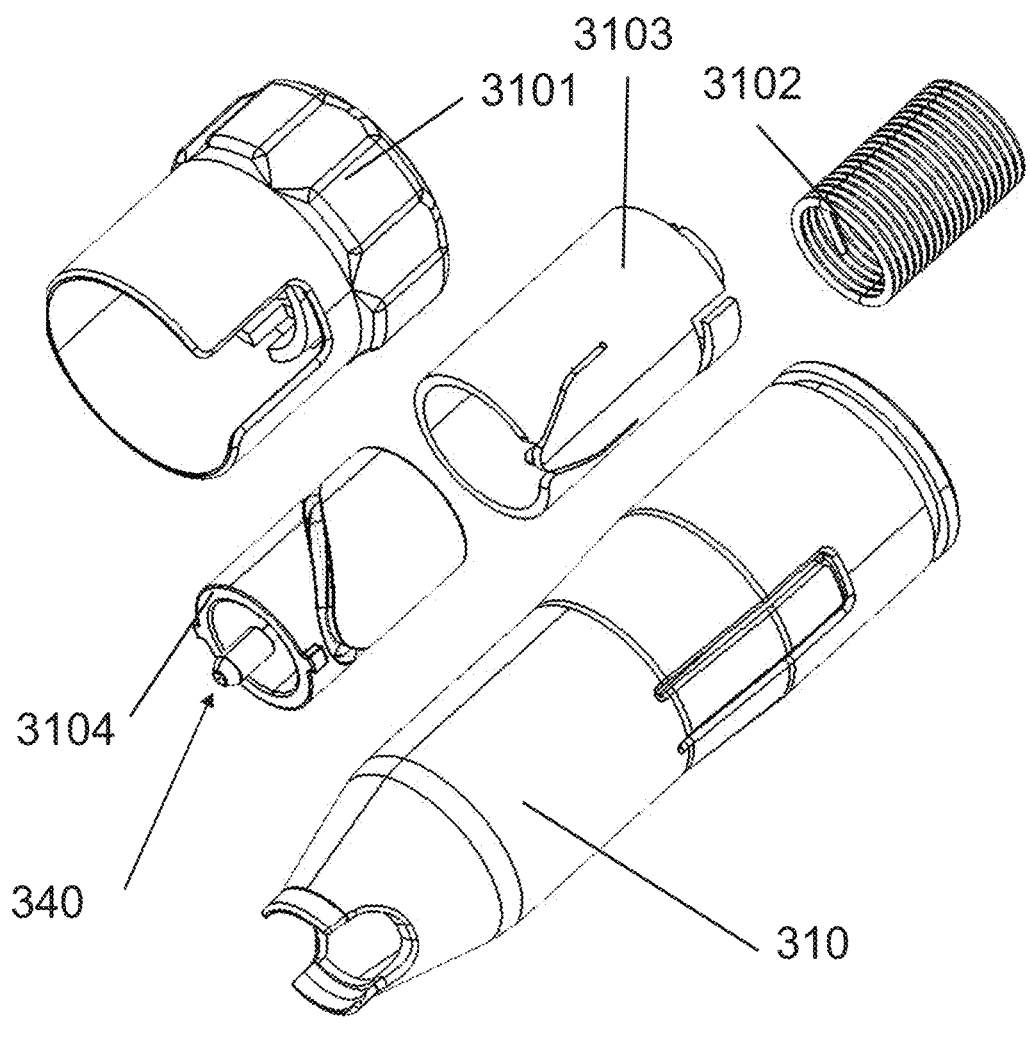
FIG. 14 schematically illustrates a perspective view of parts of the reusable inserter.

FIG. 14 illustrates schematically a perspective view of parts of the reusable inserter 30. The reusable inserter 30 comprises a housing 310. The reusable inserter 30 comprises a tensioning knob 3101. The reusable inserter 30 comprises a drive spring 3102. The reusable inserter 30 comprises a drive bushing 3103. The reusable inserter 30 comprises a crank 3104, which comprises a plunger 340. The crank 3104 is configured as a non-rotating part. The tensioning knob 3101, the drive spring 3102, the drive bushing 3103, and the crank 3104 can be parts of the tensioning equipment of the reusable inserter 30.

Figure 15:
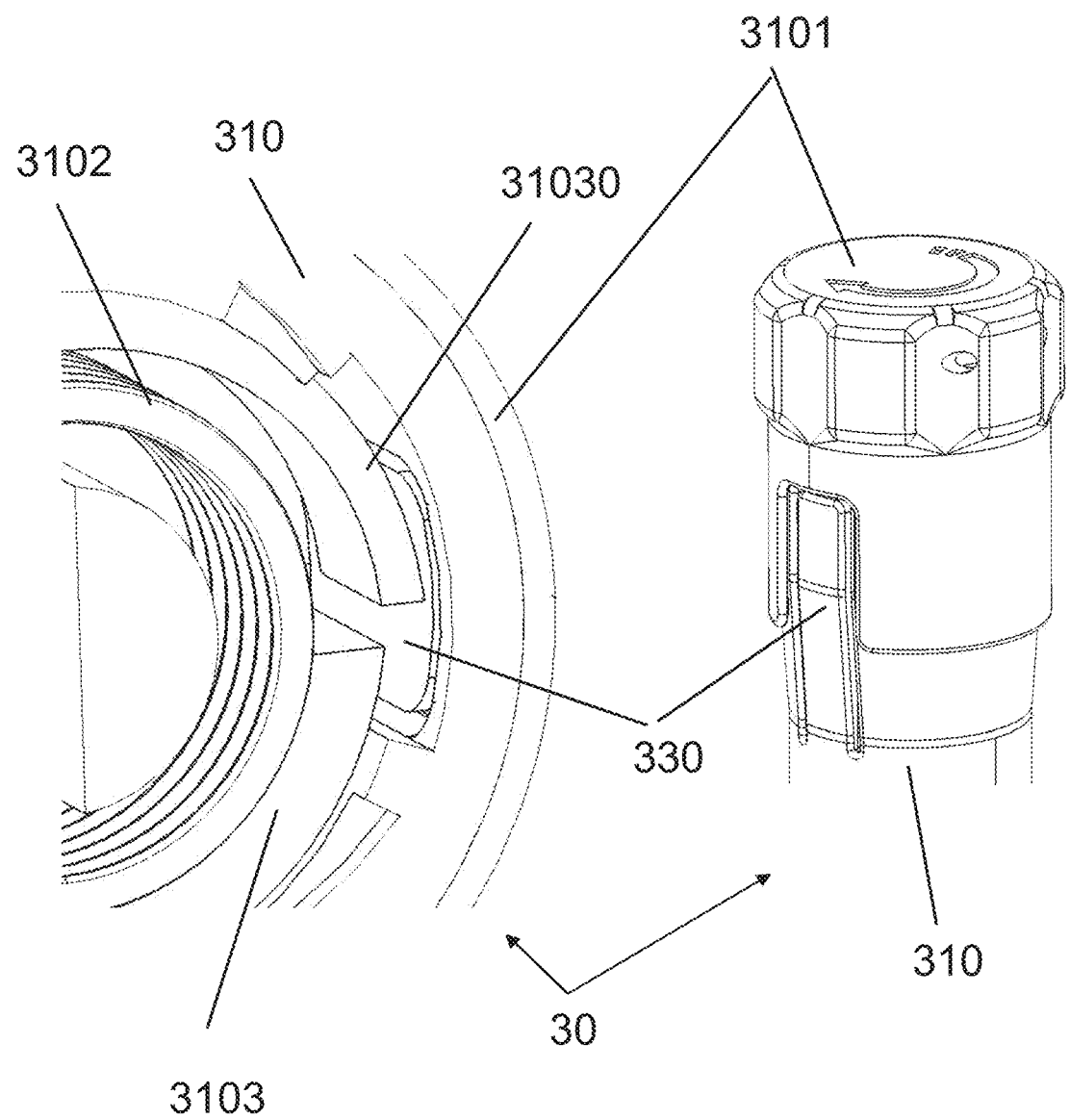
FIG. 15 schematically illustrates a sectional view (on the left of FIG. 15) of the reusable inserter and a perspective view (on the right of FIG. 15) of the reusable inserter.

FIG. 15 illustrates schematically a sectional view (on the left of FIG. 15) of the reusable inserter 30 and a perspective view (on the right of FIG. 15) of the reusable inserter 30. The reusable inserter 30 comprises a drive spring 3102 and a drive bushing 3103, which are arranged in the housing 310. The reusable inserter 30 comprises a tensioning knob 3101. The reusable inserter 30 comprises a release 330. The release 330 can interact with a latch 31030 of the drive bushing 3103. The patient can push the release 330, which moves the latch 31030 of the drive bushing 3103 towards a center of the reusable inserter 30, wherein the drive spring 3102 displaces the drive bushing 3103 in order to displace the plunger 340 and the inserter assembly 310 from a retracted position to an advanced position, wherein the cannula is inserted automatically into the skin of the patient.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERALS

10 disposable inserter
110 housing
111 locking element
1110 torsion joint
1111 lower end of locking element
1112 upper end of locking element
112 coupling arrangement
113 outlet port
115 guiding groove
120 manually operable member
130 inserter assembly
1310 cannula assembly
1311 cannula
1312 cannula hub
1320 needle assembly
1321 needle
1322 needle hub
1330 coupling assembly
20 baseplate
210 well of baseplate
30 reusable inserter
310 housing
320 tensioning equipment
3101 tensioning knob
3102 drive spring
3103 drive bushing
3104 crank
330 release
340 plunger
3101 tensioning knob

What is claimed is:

1. A disposable inserter, comprising:
    a housing;
    an inserter assembly moveable relative to the housing from a retracted position to an advanced position, the inserter assembly comprising a cannula assembly with a cannula;
    a manually operable member having an exterior surface that is accessible for a user's hand to contact and thereby move the manually operable member by hand relative to the housing, wherein the user manually moving the manually operable member moves the inserter assembly from the retracted position to the advanced position to thereby manually insert the cannula into skin of a patient;
    a lock configured to block or enable movement of the inserter assembly; and
    a coupling arrangement configured to couple the disposable inserter to a reusable inserter configured for automatically moving the inserter assembly from the retracted position to the advanced position to thereby automatically insert the cannula into the skin of the patient.

2. The disposable inserter according to claim 1, wherein the housing has an outlet port configured to engage with a baseplate of an infusion system, the baseplate configured to be adhered to the skin of the patient, and wherein the cannula assembly is configured to be placed through the outlet port into a well of the baseplate when the inserter assembly is moved from the retracted position to the advanced position to thereby insert the cannula into the skin of the patient.

3. The disposable inserter according to claim 1, wherein the lock is configured to block movement of the inserter assembly when the disposable inserter is not engaged with a baseplate of an infusion system, and the lock interacts with the baseplate when the disposable inserter is engaged with the baseplate of the infusion system to enable movement of the inserter assembly.

4. The disposable inserter according to claim 3, wherein the lock is connected to the housing of the disposable inserter via a torsion joint, wherein the lock is configured to move as a function of whether the disposable inserter engages the baseplate of the infusion system.

5. The disposable inserter according to claim 1, wherein the inserter assembly includes a needle assembly with a needle, wherein the needle assembly is configured to engage with the cannula assembly, wherein insertion of the cannula into the skin of the patient is facilitated by the needle.

6. The disposable inserter according to claim 5, wherein the needle assembly is retractable from the advanced position to the retracted position while the cannula remains in the skin of the patient, whereby the needle is retracted from the skin of the patient.

7. The disposable inserter according to claim 1, wherein the inserter assembly comprises a coupling assembly configured to couple the inserter assembly to the reusable inserter.

8. The disposable inserter according to claim 1, wherein the housing comprises an elongate body.

9. The disposable inserter according to claim 1, wherein the manually operable member comprises a manually displaceable sleeve that is displaceable along the housing and engages the inserter assembly to move the inserter assembly from the retracted position to the advanced position.

10. The disposable inserter of claim 1, wherein when the disposable inserter is coupled to the reusable inserter, the manually operable member is covered by the reusable inserter and is inaccessible for manual operation.

11. The disposable inserter of claim 1, wherein when the disposable inserter is coupled to the reusable inserter, the disposable inserter is positioned substantially inside the reusable inserter.

12. The disposable inserter of claim 1, wherein the manual movement of the manually operable member is in the insertion direction of the cannula.

13. The disposable inserter of claim 1, wherein when the disposable inserter is coupled to the reusable inserter, the manually operable member is inaccessible for manual operation.

14. An insertion system, comprising:
a disposable inserter, comprising:
  a housing;
  an inserter assembly moveable relative to the housing from a retracted position to an advanced position, the inserter assembly comprising a cannula assembly with a cannula;
  a manually operable member configured to move the inserter assembly from the retracted position to the advanced position to thereby manually insert the cannula into skin of a patient; and
  a lock configured to block or enable movement of the inserter assembly;
a coupling arrangement; and
a reusable inserter coupleable to the disposable inserter via the coupling arrangement, the reusable inserter configured to automatically move the inserter assembly from the retracted position to the advanced position to thereby automatically insert the cannula into the skin of the patient;
wherein, when the reusable inserter is uncoupled and removed from the disposable inserter, an exterior surface of the manually operable member is accessible for a user's hand to contact and thereby move the manually operable member by hand relative to the housing;
further wherein, when the disposable inserter is coupled to the reusable inserter, the manually operable member is covered by the reusable inserter and is inaccessible for gripping by the user.

15. The insertion system of claim 14, wherein the reusable inserter comprises a release configured to activate a drive for automatically displacing the inserter assembly from the retracted position to the advanced position.

16. The insertion system according to claim 15, comprising tensioning equipment configured to tension a drive spring of the drive.

17. The insertion system according to claim 16, wherein the tensioning equipment comprises a tensioning knob configured to be turned to a predefined angle for tensioning the drive spring of the drive.

18. The insertion system according to claim 17, wherein the predefined angle is about 360°.

19. The insertion system according to claim 16, wherein the tensioning equipment includes a return stop.

20. The insertion system of claim 15, wherein the reusable inserter is coupleable to the disposable inserter before, while or after the drive spring is tensioned.

21. The disposable inserter of claim 14, wherein when the disposable inserter is coupled to the reusable inserter, the disposable inserter is positioned substantially inside the reusable inserter.

22. A disposable inserter, comprising:
a housing;
an inserter assembly arranged in the housing and moveable relative to the housing from a retracted position to an advanced position, the inserter assembly comprising a cannula assembly with a cannula;
a manually operable member having an exterior surface that is accessible for a user to grip from outside of the housing and thereby move the manually operable member relative to the housing, wherein the user manually moving the manually operable member moves the inserter assembly from the retracted position to the advanced position to thereby manually insert the cannula into skin of a patient;
a lock configured to block or enable movement of the inserter assembly; and
a coupling arrangement configured to couple the disposable inserter to a reusable inserter configured for automatically moving the inserter assembly from the retracted position to the advanced position to thereby automatically insert the cannula into the skin of the patient.

23. The disposable inserter of claim 22, wherein the manual movement of the manually operable member is in the insertion direction of the cannula.

24. The disposable inserter of claim 22, wherein when the disposable inserter is coupled to the reusable inserter, the manually operable member is inaccessible for manual operation.

* * * * *